United States Patent
Novikau et al.

(10) Patent No.: US 10,031,327 B2
(45) Date of Patent: Jul. 24, 2018

(54) METHOD FOR HIGH-RESOLUTION 3D-LOCALIZATION MICROSCOPY

(71) Applicant: Carl Zeiss Microscopy GmbH, Jena (DE)

(72) Inventors: Yauheni Novikau, Jena (DE); Thomas Kalkbrenner, Jena (DE)

(73) Assignee: Carl Zeiss Microscopy GmbH, Jena (DE)

( * ) Notice: Subject to any disclaimer, the term of this patent is extended or adjusted under 35 U.S.C. 154(b) by 385 days.

(21) Appl. No.: 14/133,169

(22) Filed: Dec. 18, 2013

(65) Prior Publication Data
US 2014/0176678 A1     Jun. 26, 2014

(30) Foreign Application Priority Data

Dec. 21, 2012 (DE) .......... 10 2012 224 306

(51) Int. Cl.
| | |
|---|---|
| G02B 21/16 | (2006.01) |
| G01N 21/64 | (2006.01) |
| G02B 21/36 | (2006.01) |
| G02B 27/58 | (2006.01) |

(52) U.S. Cl.
CPC .......... *G02B 21/16* (2013.01); *G01N 21/6458* (2013.01); *G02B 21/367* (2013.01); *G02B 27/58* (2013.01)

(58) Field of Classification Search
None
See application file for complete search history.

(56) References Cited

U.S. PATENT DOCUMENTS

| | | | | |
|---|---|---|---|---|
| 5,389,101 | A * | 2/1995 | Heilbrun | A61B 5/06 348/E13.014 |
| 9,213,176 | B2 * | 12/2015 | Pertsinidis | G02B 21/18 |
| 2008/0068588 | A1 | 3/2008 | Hess et al. | |
| 2010/0231922 | A1 * | 9/2010 | Hess | G01B 9/04 356/496 |

FOREIGN PATENT DOCUMENTS

| | | |
|---|---|---|
| DE | 10 2006 021 317 A1 | 10/2007 |
| DE | 10 2008 021 641 A1 | 11/2009 |

(Continued)

OTHER PUBLICATIONS

German Search Report dated May 28, 2014.
(Continued)

*Primary Examiner* — Janese Duley
(74) *Attorney, Agent, or Firm* — Duane Morris LLP

(57) ABSTRACT

A method for high-resolution 3D-localization microscopy of a sample having fluorescence emitters, in which the fluorescence emitters are excited to emit fluorescent radiation and the sample is displayed with spatial resolution in widefield microscopy. Excitation is caused such that at least some fluorescence emitters are isolated. A three-dimensional localization is determined in a localization analysis, which includes a z-coordinate, x-coordinate as well as a y-coordinate orthogonal thereto, for each isolated fluorescence emitter. A table of localization imprecision is provided. Localization imprecision being determined for each localized fluorescence emitter by accessing the table of localization imprecision.

6 Claims, 3 Drawing Sheets

(56) References Cited

FOREIGN PATENT DOCUMENTS

| | | | |
|---|---|---|---|
| DE | 10 2009 060 490 A1 | 6/2011 | |
| JP | 2007-140322 A | 6/2007 | |
| JP | 2008-309603 A | 12/2008 | |
| JP | 2011-059100 A | 3/2011 | |
| JP | 2011-514532 A | 5/2011 | |
| WO | WO 2006/127692 | 11/2006 | |
| WO | WO 2006/127692 A2 | 11/2006 | |
| WO | WO 2009/115108 A1 | 9/2009 | |

OTHER PUBLICATIONS

German Search Report dated Feb. 15, 2013.

Betzig, Eric et al., "Imaging Intracellular Fluorescent Proteins at Nanometer Resolution", Science 2006, 313:1642-1645.

Thompson, Russell et al., "Precise Nanometer Localization Analysis for Individual Fluorescent Probes", Biophysical Journal 2002, 82(5):2775-2783.

Williamson, David J. et al., "Pre-existing clusters of the adaptor Lat do not participate in early T cell signaling events", Nature Immunology 2011, 12(7):655-662.

Huang, Bo et al., "Three-Dimensional Super-Resolution Imaging by Stochastic Optical Reconstruction Microscopy", Science 2008, 319:810-813.

Pavani, et al., "Three-dimensional, single-molecule fluorescence imaging beyond the diffraction limit by using a double-helix point spread function",PNAS 2009,106(9):2995-2999.

Shtengel, Gleb et al., "Interferometric fluorescent super-resolution microscopy resolves 3D cellular ultrastructure", PNAS 2009, 106(9):3125-3130.

Toprak, Erdal et al., "Three-Dimensional Particle Tracking via Bifocal Imaging", Nano Letters 2007, 7(7):2043-2045.

Juette, Manuel F. et al., "Three-dimensional sub-100 nm resolution fluorescence microscopy of thick samples", Nature Methods 2008, 5(6):527-529.

Baddeley, David et al., "Visualization of Localization Microscopy Data", Microscopy & Microanalysis 2010, 16:64-72.

Baddeley, et al.,"4D Super-Resolution Microscopy with Conventional Fluorophores and Single Wavelength Excitation in Optically Thick Cells and Tissues",PlosOne 2011,6(5):e20645.

Mlodzianoski, Michael J. et al., "Sample drift correction in 3D fluorescence photoactivation localization microscopy", Optics Express 2011, 19(16):15009-15019.

Mortensen, Kim I. et al., "Optimized localization analysis for single-molecule tracing and super-resolution microscopy", Nature Methods 2010, 7(5):377-381.

Owen, Dylan M. et al., "PALM imaging and cluster analysis of protein heterogeneity at the cell surface", Journal of Biophotonics 2010, 3(7):446-454.

English translation of the Japanese Office Action dated Nov. 7, 2017 submitted with the Information Disclosure Statement filed on Dec. 5, 2017.

Japanese Office Action dated Nov. 7, 2017.

\* cited by examiner

METHOD FOR HIGH-RESOLUTION 3D-LOCALIZATION MICROSCOPY

RELATED APPLICATIONS

The present application claims priority benefit of German Application No. DE 10 2012 224 306.2 filed on Dec. 21, 2012, the contents of which are incorporated by reference in its entirety.

FIELD OF THE INVENTION

The invention relates to a method for high-resolution 3D-localization microscopy of a sample comprising fluorescence emitters, in which the fluorescence emitters in the sample are excited to emit fluorescent radiation and the sample is displayed with local resolution in wide-field microscopy, with the excitation being caused such that in reference to the local resolution at least some fluorescence emitters are isolated, and in a localization analysis a three-dimensional localization is determined, which includes in the depth direction of the display a z-coordinate and a x-coordinate as well as a y-coordinate orthogonal in reference thereto, for each isolated fluorescence emitter with a precision which exceeds the local resolution.

The invention further relates to a high-resolution microscope for 3D-localization microscopy of a sample comprising a fluorescence emitter, showing an excitation device, which is embodied to excite the fluorescence emitters in the sample to emit fluorescent radiation, and a display device, embodied to display the sample with a local resolution, with the excitation device being embodied such that at least some fluorescence emitters are isolated in the display in reference to the local resolution, and the microscope comprises a device for analyzing localization, which is embodied to determine a three-dimensional location, comprising in the depth direction of the display a z-coordinate and a x-coordinate and a y-coordinate orthogonal in reference thereto, for each fluorescence emitter with a precision exceeding the local resolution.

BACKGROUND OF THE INVENTION

Various methods have been developed in the prior art to overcome the diffraction limits in microscopy. From WO 2006/127692 or DE 102006021317 A1 a method with the abbreviation PALM (photo activated localization microscopy) is known, which uses a marker substance for displaying a sample, which can be activated e.g., via optic radiation. The marker substance can emit certain fluorescent radiation only in the activated state. Non-activated molecules of the marker substance emit none or at the most no detectable fluorescent radiation, even after exciting radiation impacting them.

Accordingly the activating radiation is generally called the switching signal. In the PALM-method the switching signal is applied such that at least a certain portion of the activated marker molecules are distanced from neighboring activated molecules such that these marker molecules can be separated, measured by the optic resolution of microscopy, or subsequently separated by image processing. Here, it is assumed that a portion of the fluorescence emitters are isolated. After accepting the fluorescent radiation, the center of their distribution of radiation is then determined for these isolated emitters, to a limited extend as caused by the resolution. Based thereupon, by way of calculation the position of the molecules can be determined with higher precision than actually possible based on the optic resolution. This process is called localization. The increased resolution by determining focal points of the distribution of diffraction by way of calculation is also called "super resolution" in the professional English literature. It requires that in the sample at least a portion of the activated marker molecules can be distinguished using optic resolution, thus they are isolated. Then their position can be determined with higher precision; they can be localized.

In order to isolate individual marker molecules the PALM principle uses statistic effects. In a marker molecule, which upon receipt of the switching signal of a predetermined intensity can be excited to emit fluorescent radiation, it can be ensured by adjusting the intensity of the switching signal that the probability to activate marker molecules present in a given area of the sample is so low that there are sufficient sections in which, within the optic resolution, only marker molecules that can be distinguished emit fluorescent radiation.

The PALM principle was further developed with regards to the activation of the molecules to be detected. For example, in molecules showing a long-term non-fluorescent state and a short-term fluorescent state, any separate activation with activating radiation, which can be spectrally distinguished from the exciting radiation, is not required at all. Rather, the sample is first activated with an illuminating radiation of high intensity so that the overwhelming portion of the molecules has been brought into the non-fluorescent long-term state (e.g., a triplet state). The remaining molecules still fluorescing are this way isolated with regards to the optic resolution.

It shall also be mentioned that the PALM-principle has been identified in professional literature with different abbreviations, such as STORM etc. In the present description the abbreviation PALM is used for all microscopic imagery achieving localization exceeding the optic resolution of the device used, by first isolating fluorescent molecules and then localizing them.

The PALM-method is advantageous in that no high localization is required for the illumination. A simple wide-field illumination is possible.

The PALM-principle requires that many individual images are recorded from the sample, each of which respectively including portions of the isolated molecules. In order to display the sample in its entirety the quantity of all individual images must ensure that all molecules have been included in said portions at least once, to the extent possible. Accordingly, the PALM-method regularly requires a plurality of individual images, which leads to a certain duration being necessary for recording an overall image. This leads to considerable computing expenses, because in each individual image a plurality of molecules must be localized by way of calculation. Here, large quantities of data develop.

This precision of localization is achieved only laterally by the localization in the individual images, thus in a single level, which is allocated to the image level of the camera. The methods are therefore restricted in this regard to a two-dimensional sample analysis. Accordingly, the PALM-principle has been combined with TIRF-excitation, which ensures that only fluorophores from a thin layer of the sample are emitting.

One of the important parameters in the PALM-method is the imprecision of localization. It represents a positioning error, by which the respectively detected fluorescence emitter is shown in the final image. This imprecision of localization is a considerable factor, in particular when structures shall be found in this image in a subsequent processing step.

The scientific literature has therefore discussed the question from a very early time on, how the precision of localization can be determined. The publication Betzig et al., Science 313, 1642-1645, 2006, allocates a 2D-Gauβ-distribution to each localized fluorescence emitter with regards to the localization, with its standard deviation being equivalent to the determined positioning error. The precision by which a fluorescence emitter can be localized two-dimensionally has been deducted in the publication Thompson et al., Biophysical Journal 82, 2775, 2002, as a function of the pixel size, the photon count, and the intensity of the background radiation (in prior art also called background fluctuation). Further, the imprecision of the localization depends on the final size of the pixel confusion function as well as the pixeling of the sensor. The deduction disclosed in this publication was criticized in prior art as an overly optimistic approximation, i.e. as an approximately predicting localization with insufficient precision. In this regard, reference is made to the publication Williamson et al., Nature Immunology 12, 655, 2011. However it is particularly problematic that the statements made regarding the imprecision of localization can exclusively be used for the two-dimensional localization microscopy.

Accordingly it cannot be used for further developments of localization microscopy, which allows using luminescent marker molecules also in the third spatial direction, representing the depth direction in reference to the display of the sample. For this purpose, approaches are also known from prior art. Here, "depth direction" is understood as the direction longitudinal in reference to the incident light, thus longitudinal in reference to the optic axis.

The publication B. Huang et al., Science 319, page 810, 2008 describes an imagery radiation path for the PALM-principle, in which a weak cylinder lens is located, leading to a targeted astigmatic distortion. In this way the image of the molecule is elliptically distorted on the camera as soon as the molecule is located above or below the focal level, thus the point of symmetry of the pixel confusion function. From the orientation and the extent of distortion the information about the depth location of the luminescent marker molecule can be acquired. A disadvantage of this method lies in the fact that the local environment and the orientation of a molecular dipole may also lead to a distortion of the image of the luminescent marker molecule, not at all connected to the depth location. Such luminescent marker molecules are then allocated to a wrong depth value, depending on their orientation.

The publication Pavani et al., PNAS 106, page 2995, 2009 suggests modifying the pixel confusion function by a spatial phase modulator in the image to form a double helix structure. The pixel images of individual luminescent marker molecules are then coded into double spots, their depth location being in the angular orientation of the joint axis of said double spots.

According to the publication of Shtengel et al., PNAS 106, page 3125, 2009 photons emitted by the luminescent marker molecules interfere with themselves. For this purpose two lenses assembled in a 4π-configuration are used, which simultaneously observe the luminescent marker molecules. The partial radiation paths obtained in this way are made to interfere via a particular three-path beam splitter. Each of the images obtained here is detected by a camera. The intensity ratios of the images allow conclusions about the depth location.

The publications Toprak et al., Nanolet. 7, pages 3285-3290, 2007 as well as Juette et al., Nature Methods 5, page 527, 2008, describe an approach in which a 50/50 beam splitter is installed in the imaging radiation path, which splits the image of the sample into two partial images. These two images are detected independently.

Additionally, in one of the partial radiation paths obtained here, an optic path length difference is introduced such that two object levels result from the two partial radiation paths, which are separated from each other, for example, by a half or an entire optic minimum resolution (for example 700 nm) in the z-direction, thus the depth direction. The depth position of marker molecules located between these two levels can now be determined by analyzing the two partial images of the same marker molecule (e.g., with regards to the width of the pixel confusion image) or by appropriate fitting of a three-dimensional pixel confusion function. The method requires two partial high-resolution images and a precise adjusting of the radiation paths and calibration measurements in order to achieve a sub-pixel precise interference of the two partial images. Further, the two partial images of a marker molecule generally show a different form because the lateral extension of the pixel confusion function of a displaying system changes depending on the location of the observed object level.

DE 102009060490 A1, which for the rest also lists further literature references regarding 3D-high resolution, also follows the generic approach according to Toprak et al., i.e. to split the image of the sample into two partial images.

Additional literature for high-resolution localization microscopy and particularly also 3D-localization is found in: Baddeley et al., Microscopy & Microanalysis 16, 64, 2010; Baddeley et al., PlosOne 6, e20645, 2011; Juette et al., Nature Methods 5, 527, 2008, Mlodzianoski et al., Optics Express 19, 15009, 2011; Mortensen et al., Nature Methods 7, 377, 2010; Owen et al., Journal of BioPhotonics 3, 446, 2010.

OBJECT OF THE INVENTION

The invention is based on the objective to provide a method for determining the imprecision of localization of isolated fluorescence emitters, which is also suitable for three-dimensional localization microscopy.

The objective is attained in a first variant of the invention by a method for high-resolution 3D-localization microscopy of a sample comprising fluorescence emitters, in which the fluorescence emitters in the sample are excited in order to emit fluorescent radiation and the sample is displayed with a spatial resolution in the wide-field microscopy, the excitation is caused such that in reference to the spatial resolution at least some fluorescence emitters are isolated, and in a localization analysis a three-dimensional spatial resolution is determined for each isolated fluorescence emitter with a precision, which comprises in the depth direction of the display a z-coordinate and orthogonally thereto a x-coordinate and a y-coordinate for each isolated fluorescent emitter with a precision exceeding the spatial resolution, with a table of localization imprecision being provided, which states the imprecision of the spatial resolution, namely at least with regards to the z-coordinate as a function of the z-coordinate and a plurality of photons collected during the imaging in the wide-field microscopy, and for each localized fluorescence emitter a spatial resolution imprecision is disclosed by accessing the table of spatial resolution imprecision for the spatial resolution determined in the localization analysis.

The objective is solved in a second variant in a method for high-resolution 3D-localization microscopy of a sample comprising fluorescence emitters, in which the fluorescence emitters in the sample are excited to emit fluorescent radiation and the sample is displayed with a spatial resolution in wide-field microscopy, with the excitation being caused such that in reference to the spatial resolution at least some fluorescence emitters are isolated and in a localization analysis a three-dimensional localization is determined, which comprises in the depth direction of the image a z-coordinate as well as a x-coordinate and a y-coordinate orthogonal in reference thereto, for each isolated fluorescence emitter with a precision, which exceeds the spatial resolution, with an imprecision of localization being determined, which states an imprecision of the localization, namely with regards to at least its z-coordinate as a function of the z-coordinate and a plurality of photons, which were collected in the image in wide-field microscopy, and for each localized fluorescence emitter, by accessing the table of localization imprecision, a localization imprecision is determined for the localization determined in the localization analysis, with the localization imprecision being determined by way of a simulation comprising the following steps:

a) an image is simulated for an ideal, dot-shaped fluorescence emitter for the predetermined number of photons emitted by the fluorescence emitters for an image, particularly for an average number of photons, b) this simulated image is modified with a pixel confusion function to form an expanded image, with the pixel confusion function preferably being dependent on the predetermined localization of the fluorescence emitter, c) the expanded image is modified in consideration of statistic noise influences to form a noisy, expanded image, with the statistic noise influences being dependent on the number of photons, d) the expanded image is subjected to a localization analysis, in order to obtain a simulated localization from the noisy, expanded image, and e) steps b) through d) are repeated several times for various values of the statistic noise influences, a spread of the several simulated localizations obtained here or a spread of differences between these several simulated localizations and a predetermined localization is determined, and from said spread the imprecision of the predetermined localization is determined.

In the first variant the objective is also attained by a high-resolution microscope for 3D-localization microscopy of a sample comprising fluorescence emitters, which comprises an exciting device, embodied to excite the fluorescence emitters in the sample to emit fluorescent radiation, and an imaging device, embodied to display the sample with a spatial resolution, with the excitation device being embodied such that in reference to the spatial resolution at least some fluorescence emitters in the image are isolated, and the microscope shows a localization analysis device embodied to determine a three-dimensional localization, which comprises in the depth direction of the image a z-coordinate as well as a x-coordinate and a y-coordinate orthogonal in reference thereto for each isolated fluorescence emitter with a precision exceeding the spatial resolution, whereby the localization analysis device comprising a table for localization imprecision, which states the imprecision of the localization, namely at least with regards to its z-coordinates as a function of the z-coordinates and a number of photons, collected from the wide-field camera, and the localization analysis device being embodied to determine for each localized fluorescence emitter, by accessing the table of localization imprecision, a localization imprecision for the localization determined earlier.

In the first variant the invention uses a table of localization imprecision which includes an imprecision regarding at least the z-coordinate of the localization. The inventors have recognized that for this imprecision, both the z-coordinate itself, as well as the number of photons collected when displaying the respecting fluorescence emitter in the wide-field microscopy, are decisive. Both statements are known from the localization analysis for each isolated fluorescence emitter. In the second variant the localization imprecision is determined online via simulation.

The imprecision of the localization is determined by the overall system used, which includes the optic of the microscope, the wide-field imaging, and the algorithm of the localization analysis. The precision of localization achieved here can be determined experimentally, independent from assumptions or approximations, such as for example Thompson et al. required for two-dimensional analysis of the precision of localization. For this purpose, for example, fluorescing particles with a dimension smaller than predetermined by the pixel confusion function of the image used, can be excited with desired spectral features (for example, regarding the excitation and emission wave lengths) such that they provide pixels in the wide-field imagery. When such fluorescent particles are displayed repeatedly in the wide-field imagery and the localization analysis is performed in each of these images the spread of the individual localizations directly yields the localization imprecision connected to the system. Alternatively, the spread of the deviations between the individual localizations and the actual position of the particle may represent the basis for the localization imprecision.

The algorithm used in the localization analysis yields in this approach a spread depending on the number of photons contributing to an image. Accordingly, in order to provide a table of localization imprecision for an overall system, a multi-dimensional table is prepared, in which the localization imprecision is stored as a function not only for the z-coordinate but also for the photon count N, which was collected when displaying the respective fluorescence emitters in the wide-field imagery. Additional parameters of the microscopy imaging affecting the localization precision and thus potentially considered in an experimental determination as parameters of the table of localization imprecision are so-called background fluctuations, parameters describing the pixel confusion function, the x-position and y-position of the respective fluorescence emitter (in order to consider e.g., variations of the pixel confusion function depending on the location or aberrations independent from the location) or the polarization of the radiation.

The background fluctuation detects photons positioned during the localization analysis on an observed pixel, however not originating at the localized fluorescence emitter. This can relate to photons detected in the wide-field illustration although they were physically not present at all, and thus must be attributed to noise effects of the detection (e.g., of a wide-field camera). However, they can also be actual physically detected photons, which are positioned on a pixel by way of disbursing processes or the like and did not originate from the isolated fluorescence emitter—for example, coming from fluorescence emitters of other depth levels.

The table of localization imprecision can be determined experimentally. Here it is preferred that at least one calibration measurement is performed at least at one calibration body, the fluorescence emitter.

However, it is also possible to determine the localization imprecision by way of simulation, which observes the effects of the overall system upon the localization imprecision in the form of a model. This way a table of localization imprecision can already be provided (first variant) or the localization imprecision can be calculated directly (second variant). In the simulation an ideal, dot-shaped fluorescence emitter is assumed with an appropriate localization. The image of this ideal fluorescence emitter is simulated for a predetermined number of photons emitted by the fluorescence emitter per image, e.g., the average photon count. Subsequently this simulated image is modified into an expanded image with a pixel confusion function, which is equivalent to the actual microscope, to the extent possible. The pixel confusion function is here dependent on the localization, as is the case in real microscopes. The expanded image is then subjected to statistic noise influences and this way modulated to a noisy, expanded image.

The statistic noise influences are simulated such that they depend on the predetermined number of photons. The noisy, expanded image obtained here is then subjected to the localization analysis. A preferably three-dimensional localization is obtained for the noisy, expanded image. This process is repeated several times, with the first images generated slightly differ from each other due to the statistic noise influences, and accordingly the fluorescence emitters are differently localized. These multiple images, e.g., 100, lead to slightly different localizations, thus simulated localizations. Due to the fact that the photons obey with regards to the differences in the noisy individual images, e.g., by the Poisson statistic, thus are not always distributed evenly to the (simulated) pixels, and additionally, optionally the background fluctuations b in each individual image [results] in slightly different pixel brightness, here for each individual image a different localization results. The comparison of the simulated localizations with each other or with a predetermined (actual) localization yields the imprecision of said localization. After these steps were processed, one has an imprecision statement for a predetermined localization and a predetermined number of photons.

The steps are therefore repeated as needed for various predetermined numbers of photons and for various predetermined three-dimensional localizations, in order to obtain a table of localization imprecision, which covers a certain value range for the localization and the number of photons.

In order to use simulation for an experimental provision of the table of localization imprecision, a further development of the method according to the invention is therefore preferred, which comprises the following steps:

a) an image of an ideal, dot-shaped fluorescence emitter is simulated for a predetermined number of photons, emitted by the fluorescence emitter for an image, particularly for an average number of photons, b) this simulated image is modified with a pixel confusion function into an expanded image, with the pixel confusion function preferably being dependent on a predetermined localization of the fluorescence emitter, c) the expanded image is modified into a noisy, expanded image, in consideration of statistic noise influences, with the statistic noise influences being dependent on the predetermined number of photons, d) the expanded image is subjected to a localization analysis in order to obtain a simulated localization from the noisy, expanded image, and e) steps b) through d) are repeated several times for various values of the statistic noise influences, a spread of the several simulated localizations obtained from this or a spread of differences between several simulated localizations and the predetermined localization is determined, and from the spread the imprecision of the predetermined localization is determined, f) the steps a) through e) are repeated for various predetermined numbers of photons and for various predetermined three-dimensional localizations.

The consideration of the statistic noise can be realized in the simulation (according to both variants) particularly preferred by a Monte-Carlo-simulation, which interferes the noisy image. In each repetition another status of the statistic interference is used. Particularly preferred is here the evaluation of a Poisson distribution, with its (single, as is known) parameter being based on the predetermined number of photons. Here, the average photon number per localized molecule has also proven particularly beneficial. Accordingly, in every processing of the Monte-Carlo-simulation another statistic interference condition is used for modifying the noisy image, particularly with regards to the distribution of the photons on the image pixels; for example, a value is obtained according to the Poisson distribution.

The simulation mentioned can additionally consider the background noise during the wide-field detection when the simulated image or the noisy image is additionally provided with background noise equivalent to the above-mentioned background fluctuations. Here, either the image can be directly provided with background noise, or the background noise is subjected to independent, statistic noise influences and then combined with the image obtained from step b). An equivalent alternative is to provide the pixel confusion function with a portion considering the background noise.

The table of localization imprecision must understandably be suited to provide statements regarding imprecision for the entire value range of the considered parameters, which occur during a measurement. Generally speaking, it covers an n-dimensional parameter range by defining a (n-1)-dimensional surface. This surface is provided by predetermined support positions of the n-dimensional parameter range. Beneficially the number of support positions is kept as low as possible and an interpolation is performed for parameter values located between said support positions within the table of the localization imprecision. Extrapolation is possible for parameters located outside the detected value range. In order to keep errors as low as possible in this method, arising by interpolation or extrapolation, it is preferred to determine the table of localization imprecision within the localization analysis which determines the three-dimensional localization, iteratively generating, or expanding, with an iteration step always being performed when the localization analysis yields values of localizations and/or is performed for numbers of photons, which are distanced from respective support positions of the table of the localization imprecision by a certain minimum value.

Thus, when first a value range with intervals is defined for the input parameters the table for localization imprecision generates for these value ranges and intervals and always amends them when in the actual operation an interpolation or extrapolation must be performed, which would be distanced too far from the already existing support position. If this is the case, by way of simulation the table for localization imprecision is amended appropriately. This may also occur during the overall PALM image generation or data processing.

For the experimental determination of the table for localization imprecision the number of photons may be influenced by varying the power of the exciting radiation, for example a laser power of the fluorescence excitation and by a suitable selection of the fluorescence emitter. The background fluctuations can be changed by varying the angle of illumination. For example, it is possible to combine a TIRF-radiation causing little background using an EPIradiation leading to more background radiation in different compositions. Additionally a variation of the intensity of excitation and/or a wide-field illumination with white light may be used for varying the background fluctuations.

The z-position may be modified in the experimental determination of the table of localization imprecision by displacing the sample or displacing the object, thus generally by a change of the relative position of the sample in reference to the lens.

The same applies for the x-/y-position, which additionally can be varied by selecting the fluorescent emitter. By such experimental influencing, a value range of the predetermined parameters can be detected in order to generate the table of localization imprecision with sufficient density and sufficient support positions.

To the extent that processing steps are explained in the following they may be realized by an appropriate operation of the microscope comprising a suitably embodied control device. To the extent here, processing features are being described as they relate to the suitable embodiment of the control device, for example by an appropriate operating program. Inversely, of course it also applies that features of a control device, for example achieved by respective programming means, also relate to and shall disclose processing features of a respective operating method.

It is understood that the above-mentioned features, explained in the following, can be used not only in the stated combinations but also in other combinations or as stand-alone features without leaving the scope of the present invention.

BRIEF DESCRIPTION OF THE DRAWINGS

In the following the invention is explained in greater detail as an example based on the attached drawing, which disclose the features essential according to the invention. It shows.

DESCRIPTION OF THE EMBODIMENTS

Figure 1:
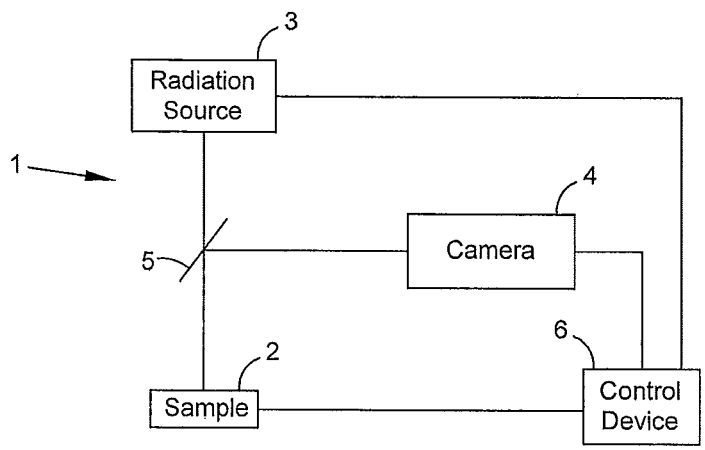
FIG. 1 is a schematic illustration of a microscope for implementing the PALM-method.

FIG. 1 shows schematically a microscope 1 displaying in high-resolution a sample 2. The term high-resolution is here used, as common in prior art, for an imaging method showing a spatial resolution exceeding the diffraction limit of the illustration. The microscope 1 serves for, displaying a sample 2, which includes fluorescent emitters. By radiation from a radiation source 3 the fluorescent emitters are excited to emit fluorescent radiation. A wide-field camera 4 displays via a beam splitter 5 the fluorescent sample 2. The operation of the microscope 1 is controlled by a control device 6, which is connected via appropriate control lines (not further identified) to a table—on which the sample 2 is located—to the wide-field camera 4 as well as the radiation source 3 and controls these elements and/or receives data from them, particularly image data from the wide-field camera.

The control device 6 is embodied such that the microscope 1 executes a localization-based microscopy method, for example the PALM-method.

Figure 2:
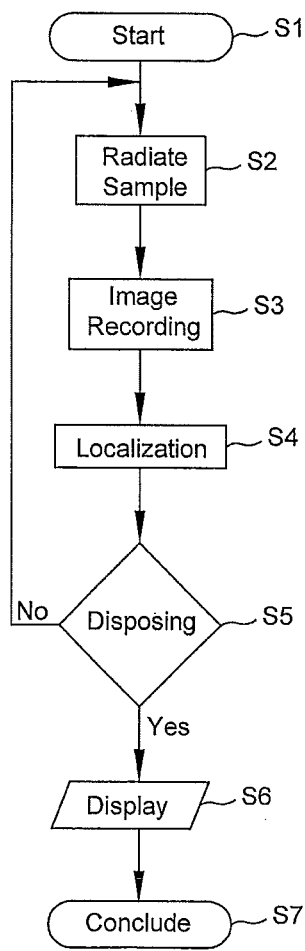
FIG. 2 is a flow chart for generating high-resolution images with the microscope of FIG. 1 in the PALM-method.

The processing executed here is shown in FIG. 2 in the form of a flow chart. After the process has been started in a step S1 the sample 2 is illuminated by the radiation source 3 in a step S2, with this occurring such that individual fluorescence emitters are isolated in reference to the spatial resolution of the image. The display occurs in a subsequent image recording step S3, which yields a wide-field image of the sample by at least individual fluorescence emitters showing a distance from neighboring fluorescence emitters, which is greater than the spatial resolution of the wide-field image.

A subsequent localization step S4 determines the localization in the image with a spatial resolution for these isolated fluorescence emitters, which is greater than the diffraction limit it actually permits. This may occur such that in the localization step S4 it is known that the radiation absorbed by an isolated fluorescence emitter originates only in one fluorescence emitter. By this knowledge the location can be determined at which the fluorescence emitter is positioned with greater precision than permitted by the diffraction limit. In a simplified manner, it can be imagined that the localization analysis occurring in the localization step S4 occurs such that the focal point is determined for the diffraction disk of an isolated fluorescence emitter, which then represents the localization. In prior art several approaches are known for such a localization analysis, e.g., including the publications mentioned in the introductory part of the description.

In step S4 the localization of the isolated fluorescence emitters is determined three-dimensionally, i.e. in a depth direction which is located in the direction of the incident radiation and/or the illustration of the sample 2, as well as a x-level/y-level aligned perpendicular in reference thereto.

In the localization step S4, in addition to the high-resolution localization, also a localization imprecision is determined, which reflects the localization error when determining the localization. In the following the determination of the localization imprecision is discussed in greater detail based on FIGS. 3 to 5.

The single execution of the localization step S4 yields one localization only for the fluorescence emitters that were essentially isolated in the previously performed imaging step S3. In order to allow deducting from the sample all fluorescence emitters to the extent possible, the steps S2 to S4 are therefore repeated several times to possibly obtain all fluorescence emitters once in the subset of the isolated fluorescence emitters. Accordingly a disposing step S5 follows the localization step S4, in which it is checked if the sample has been illustrated to a sufficient degree. For this purpose for example the plurality of localizations can be used, which had been obtained from all previous radiation processes of the localization step S4. Such an inquiry is known to one trained in the art because it is also used in PALM-methods or other localization-based high-resolution methods operating without the determination of a localization imprecision. If the sample was sufficiently detected (J-branching) the image is displayed in, a step S6.

Otherwise (M-branching) the steps S2 to S4 are repeated, whereby it is ensured that in the repeated processing all fluorescence emitters are isolated, to the extent possible. In prior art there are various options, for example the use of fluorescence emitters, which may be switched on or off with regards to their capacity for fluorescing, etc. In this context reference is made to prior art.

The most common method (being the simplest) comprises first recording the image data (and perhaps storing it) and then carrying out the processing of each individual image as described above.

After displaying the entire image in the image display step S6 the method is concluded in a step S7, and the sample 2 was illustrated with a spatial resolution exceeding the optic illustration limit, with an imprecision also being disclosed for each localization of a fluorescence emitter. This imprecision is particularly advantageous when in another step (not shown in the flow chart) structures are identified in the overall image.

As already mentioned, not only is a localization determined for the isolated fluorescence emitter in the localization step S4, but also an imprecision of said localization. This occurs at least in the z-direction, i.e. in the depth direction, preferably however also in the other two coordinates.

Figure 3:
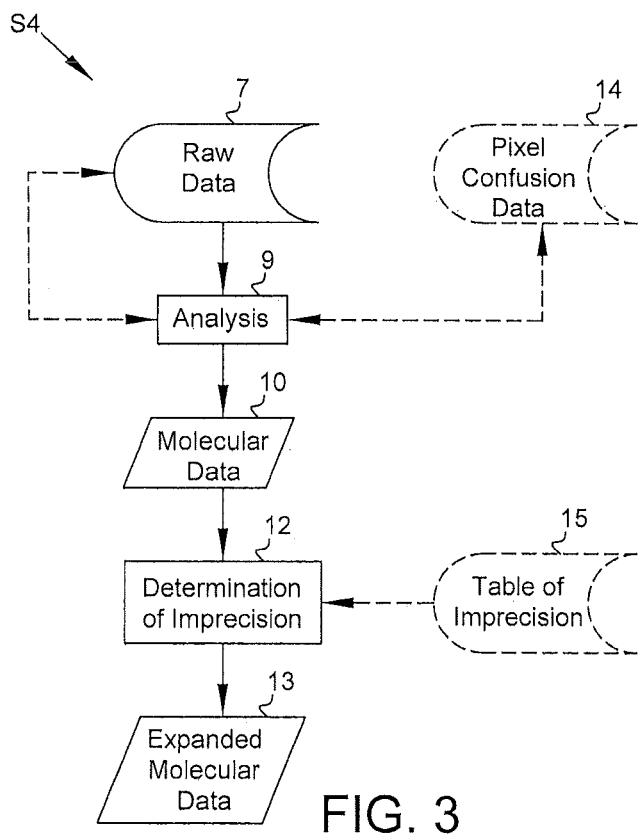
FIG. 3 is a flow chart for generating a table of localization imprecision used in the method of FIG. 2.

FIG. 3 shows a flow chart for a potential exemplary embodiment of the localization step S4. In this flow chart data access is illustrated by dot-dash double arrows. The starting point for the localization step S4 is the raw data 7 of the camera, which is provided by the previous image recording step S3. By accessing this raw data from the camera, a localization analysis 9 is performed, yielding localizations for isolated fluorescence emitters. The localization analysis 9 here always accesses pixel confusion data 14, which for example indicates the three-dimensional volume that can be resolved by the microscope 1.

As a result of the localization analysis 9 molecular data 10 is obtained, the localizations of which indicate isolated fluorescence emitters. The molecular data 10 further includes for each isolated fluorescence emitter, i.e. for each identified localization, the number N of the photons used to determine the localization of precisely this very fluorescence emitter. The number N of the photons is known from the localization analysis 9; generally it is already included in the raw data 7 of the camera, indicating for each pixel how many photons have been collected here.

Further, the photon count is known as a result of the localization analysis 9, which describes background fluctuations b. Generally this represents an average photon count, which is detected for each isolated photon emitter but cannot be attributed to radiation from said fluorescence emitter. They may also represent virtual photons, that is, photons which based on noise processes during the photon detection are indicated as being detected; or real, photons not originating in the isolated fluorescence emitters due to distribution processes amongst others, however were erroneously detected in the volume allocated to this fluorescence emitter. The molecular data 10 therefore include localizations as well as the number N of photons and background fluctuations b regarding the photon count, and this for each isolated fluorescence emitter. The data regarding the background fluctuations b can be waived, here.

In a subsequent determination of imprecision 12, at least based on the z-coordinate and the number N of the collected fluctuations, the localization precision is determined with regards to the z-coordinate. This optionally occurs also based on the x-coordinate and the y-coordinate, if one intends to avoid using the optimistic formula according to Thompson et al. The background fluctuations b are also used. However they may be waived.

In the determination of imprecision 12 the table 15 is accessed, which displays a localization precision based on the above-mentioned input parameters. This generally represents absolute localization imprecision. However, relative localization precision in reference to the distance from the absolute zero or another functionally defined localization precision is possible as well. This depends on the design and structure of the table 15.

The result of the determination of imprecision 12 includes expanded molecular data 13. It differs from the molecular data 10 by the statement of imprecision, at least for the z-coordinate, optionally for the x-coordinate and/or the y-coordinate of the localization of the respective fluorescence emitter.

The table 15, which is used in the method according to FIG. 3, may be determined via experiments. In the following this is explained based on FIG. 4. Alternatively or complementary, the table 15 can also be obtained by way of simulation. This is possible both as a complete replacement of the experimental generation as well as with regards to a supplement of an experimentally determined base table, when in the method it is recognized that the density of support positions or the area of support positions of the experimentally determined table 15 is insufficient.

The experimental generation of the table is explained in the following based on FIG. 4, the simulation-based generation of the table based on FIG. 5.

Figure 4:
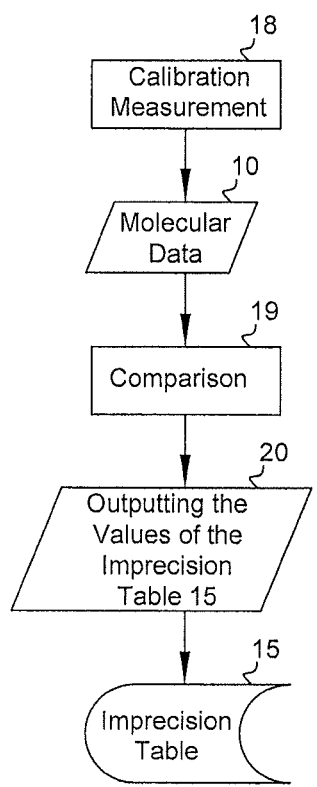
FIG. 4 is a flow chart for a method for experimentally determining the table of localization imprecision.

FIG. 4 shows a flow chart for the experimental determination of the values for the table 15. Before starting this process the parameter range and the value range are determined for the table 15. For example, in the description of FIG. 4 it is assumed that the table 15 includes the parameters z, N, and b, as well as the z-coordinate, the number of photons accepted by the isolated fluorescence emitters, and a measure for the background fluctuations. The value range for these parameters is selected such that in later measurements values expected are covered here. Further, the intervals for the value range are determined, with this occurring in consideration of the experimentally available adjustment options.

Then, as already explained in the general part of the description, a calibration body is prepared for a calibration measurement 18, comprising fluorescent particles with an extension considerably smaller than the smallest structure resolved by the microscope used. The fluorescent particles therefore show an extension below the pixel confusion function. Known fluorescent particles are particularly the so-called quantum dots. Due to the fact that an upper limit for the extension of the fluorescent particles is known, they show a known spatial extension. Further, the localization of these particles is precisely known.

In the calibration measurement 18 the calibration body is repeatedly recorded. In each of these wide-field images obtained the localization for the fluorescent emitters is yielded in a localization step S3, which is a component of the calibration measurement 18. The fluorescent emitters are further isolated in the calibration body.

This way, molecular data 10 is yielded for the fluorescent particles, namely for each individual image recorded during the calibration measurement 18. The values for the table 15 can then be determined by comparing the localizations yielded in the molecular data 10 for each individual image and a comparison with known localizations. Alternatively it is also possible to yield the data of the table 15 such that the molecular data of the individual images are only compared to each other in order to determine standard deviations of the localizations. In this alternative it is not necessary at all to know the actual localization of the fluorescent particles. Here, it is only required for the calibration body that the fluorescent particles show a spatial expansion below the resolution limit of the microscope. Alternatively, (see above) a comparison may occur with the actual localization.

The comparison of the molecular data shows in all cases of the experimentally executed method that for each isolated fluorescence emitter, realized in the described exemplary embodiment by fluorescent particles, the localizations, regarding which the table 15 shall disclose the imprecision (at least for the z-coordinate), are [sic] compared with the recorded individual images or with the known actual localization in the calibration body.

The calibration measurement 18, the generation of molecular data 10, and the comparison 19 are performed in the defined parameter range for all predetermined support positions of the value range. In order to modify the respective values by experimental modifications of the microscopy, reference is made to the general part of the description, which has already mentioned the respective measures and means.

At the end of the process according to FIG. 4 the table 15 is obtained, which is used to determine imprecision 12 in FIG. 3.

If values of the parameter range occur here which show no support positions in table 15, it is interpolated and/or extrapolated within the table 15. The table 15 can also be obtained partially or entirely by way of simulations.

Figure 5:
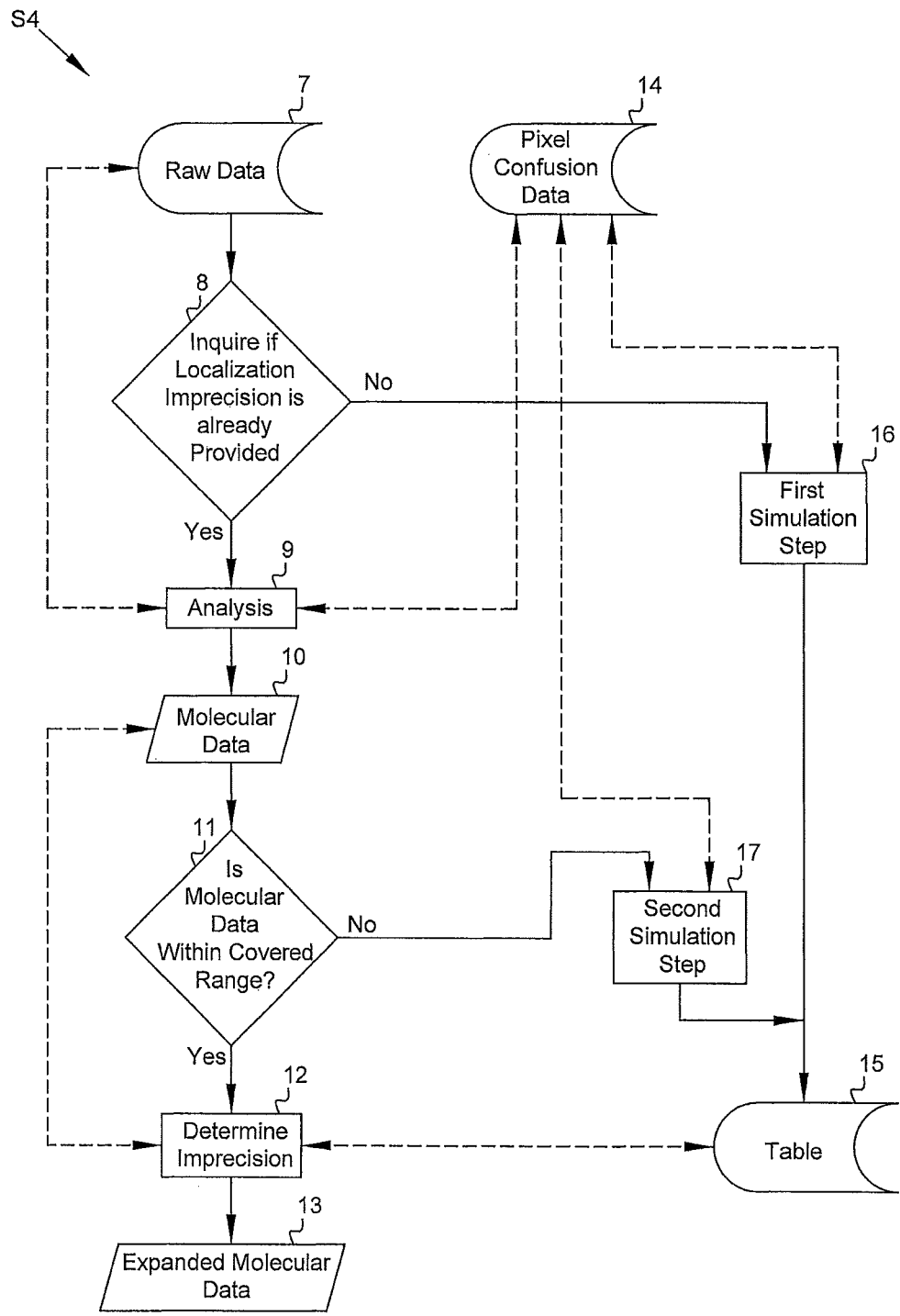
FIG. 5 is a flow chart for generating the table at least partially via a simulation alternatively or complementary to the method according to flow chart no. 4.

FIG. 5 shows a corresponding flow chart, in which elements e.g., data etc. are equivalent to those of FIG. 4, use the same reference characters.

The flow chart of FIG. 5 shows in detail the step S4 of FIG. 2, thus the localization step. It is based on the camera raw data 7 generated during imaging. First it is checked in a step 8 if the table for stating the localization imprecision is already provided. If that is not the case (N-branch) processing continues in a simulation 16, which is explained in the following. It also accesses the image confusion data 14 and generates the table 15. Due to the fact that in this state initially no table was provided, the table is allocated with a predetermine value range in the predetermined parameter range and a predetermined density of support positions and/or (appropriately) generated.

If the inquiry 8 shows that a table is already provided, the J-branching is processed for the localization analysis. The table 15 may already be present, either because it was previously generated in a simulation (e.g., the step 16 was already performed in an earlier processing of the step S4) or because a localization table was already generated experimentally.

The flow chart of FIG. 5 therefore covers both a variant in which the table 15 is generated purely based on simulations as well as embodiments in which an experimentally generated table 15 is complemented by simulations.

The localization analysis 9 accesses both the camera raw data 7 as well as the pixel confusion function 14. It yields the molecular data 10, as described above. In a step 11 it is now checked if this molecular data is within the covered value range of the table 15, i.e. the respective values at least from z to n, optionally however additionally for x, y, and b. If this is the case (J-branching) the imprecision is determined in a subsequent step 12, with here both the molecular data 10 as well as the table 15 being accessed. As a result the expanded molecular data 13 is yielded.

If the check in step 11 shows that the respective values are either entirely outside the table 15 or the nearest support position in the table 15 is too far away, a simulation is performed once more in a step 17. It is essentially equivalent to the simulation 16, however it uses a value range for the parameter range determined by the checking step 11 and the molecular data 10 underlying it. This simulation 17 also accesses the pixel confusion function 14. It complements the already provided table 16.

The simulation 16 or 17 follows the principles already described in the general part of the description.

Accordingly, first the input parameter range is determined with the respective value ranges. Subsequently for each support position, i.e. localization (at least with regards to the z-coordinate) at which one value shall be generated for the table, the image of the ideally dot-shaped emitter is simulated with a predetermined number of photons and then subjected to the pixel confusion function in order to obtain an expanded image, which considers the display features of the microscope used. This expanded image is modified in consideration of statistic noise influences to form a noisy, expanded image in which the statistic noise influences are considered depending on the number of photons. This may occur in a simulation, e.g., Monte-Carlo-simulation, as already explained in the general part of the description. The expanded, noisy image is then subjected to the localization analysis, which yields a three-dimensional localization. This process is repeated k-times for each individual set of parameters (e.g., z, N, b, x, y). Here, localizations are yielded for the simulation of a fluorescence emitter k, which are different due to statistic influences.

Consequently a cloud is yielded comprising k localizations. The cloud yields the imprecision from the comparison of the localizations with each other or with the known localization, e.g., according to stipulations of a sigma-limit or the like. These steps are now repeated for each support position of the multi-dimensional table for which said simulation shall occur. The difference between the simulations 16 and 17 is therefore essential only for the selection of the value range for which said simulation shall occur.

As an alternative for the use of a table 15, in a method similar to FIG. 5, localization imprecision allocated to each localization is calculated by way of simulation. This embodiment is equivalent to the flow chart of FIG. 5, with the modification that the checking process 8 is omitted and it is directly continued with the J-branching. The checking process 11 is also omitted. Here the N-branching is followed. Additionally the result of the simulation 17 is directly transferred into the determination of imprecision 12 without the table 15 being generated.

While the invention has been illustrated and described in connection with currently preferred embodiments shown and described in detail, it is not intended to be limited to the details shown since various modifications and structural changes may be made without departing in any way from the spirit of the present invention. The embodiments were chosen and described in order to best explain the principles of the invention and practical application to thereby enable a person skilled in the art to best utilize the invention and various embodiments with various modifications as are suited to the particular use contemplated.

What is claimed is:

1. A method for high-resolution 3D-localization microscopy of a sample having fluorescence emitters, in which the fluorescence emitters in the sample are excited to emit fluorescent radiation and the sample is displayed with spatial resolution in wide-field microscopy with excitation being caused such that in reference to the spatial resolution at least some fluorescence emitters are isolated, and in a localization analysis a three-dimensional localization is determined, which includes in a depth direction of a display a z-coordinate and a x-coordinate as well as a y-coordinate orthogonal in reference thereto, for each isolated fluorescence emitter showing a precision exceeding the spatial resolution, comprising:

providing a table of localization imprecision, which states an imprecision of the localization at least regarding its z-coordinate as a function of the z-coordinate and a number of photons collected during imaging in the wide-field microscopy, by way of simulation and by performing at least one calibration measurement of at least one calibration body, or by at least performing, without simulation, one calibration measurement of at least one calibration body, or by simulation without performing any calibration measurement and when the calibration measurement is performed the calibration measurement comprises repeatedly recording the at least one calibration body and performing at least one localization for each record, and determining a localization imprecision for each localized fluorescence emitter by accessing the table of localization imprecision for the localization determined during the localization analysis.

2. The method according to claim 1, wherein the imprecision is provided by at least performing one calibration measurement fluorescence emitters with a spatial expansion below a resolution limit of the display, and isolated in reference to said resolution limit.

3. The method according to claim 1, wherein the simulation comprises the following steps:

a) simulating an image for an ideal, dot-formed fluorescence emitter for a predetermined number of photons, b) modifying said simulated image with a point spread function to form an expanded image, with the point spread function being dependent on a predetermined location of the fluorescence emitter, c) modifying the expanded image in consideration of statistic noise influences to form a noisy, expanded image, with the statistic noise influences being dependent on the number of photons, d) subjecting the expanded image to the localization analysis in order to obtain a simulated localization from the noisy, expanded image, and e) repeating steps b) through d) several times for various values of the statistic noise influences, obtaining a spread of the several simulated localizations or a spread of differences between these several simulated localizations and the predetermined locations, and from obtaining said spread the imprecision of the simulated localizations, f) repeating steps a) through e) for various given numbers of photons and for various given three-dimensional locations.

4. The method according to claim 1, wherein said table of localization imprecision states the imprecision also as a function of at least one of the following parameters: fluctuation intensity of a background radiation detected during the imaging in the wide-field microscopy, and polarization of photons collected for the respective isolated fluorescence emitters during the imaging in the wide-field microscopy.

5. The method according to claim 1, wherein the table of localization imprecision also states the imprecision regarding the x-coordinate and the y-coordinate of the localization as a function of the x-coordinate and the y-coordinate.

6. The method according to claim 1, wherein based on the table of localization imprecision it is interpolated or extrapolated when the z-coordinate and/or the number of photons for the localized fluorescence emitter is distanced from respective values of the table of localization imprecision.

* * * * *